United States Patent [19]

Tanaka et al.

[11] Patent Number: 4,731,057

[45] Date of Patent: Mar. 15, 1988

[54] TRANSFUSION APPARATUS

[75] Inventors: Shigeru Tanaka; Tetsuya Miyatake; Yasushi Miki, all of Tokyo, Japan

[73] Assignee: Nikkiso Co., Ltd., Tokyo, Japan

[21] Appl. No.: 892,185

[22] Filed: Jul. 30, 1986

[30] Foreign Application Priority Data

Aug. 5, 1985 [JP] Japan ................... 60-171241

[51] Int. Cl.$^4$ ............................................ A61M 5/14
[52] U.S. Cl. .................... 604/153; 417/477; 604/67
[58] Field of Search ............ 604/67, 151, 153; 417/474, 475, 476, 477

[56] References Cited

U.S. PATENT DOCUMENTS

| 4,199,307 | 4/1980 | Jassnualla | 417/474 |
| 4,277,226 | 7/1981 | Archibald | 604/153 X |
| 4,373,525 | 2/1983 | Kobayashi | 417/474 |
| 4,482,347 | 11/1984 | Borsanyi | 604/153 |
| 4,493,706 | 1/1985 | Borsanyi et al. | 604/153 |
| 4,563,179 | 1/1986 | Sakai | 604/153 X |
| 4,617,014 | 10/1986 | Cannon et al. | 604/67 |

FOREIGN PATENT DOCUMENTS

| 1807979 | 7/1969 | Fed. Rep. of Germany | 604/153 |
| 57-27463 | 6/1982 | Japan . | |
| 58-165868 | 9/1983 | Japan . | |

Primary Examiner—Edward M. Coven
Attorney, Agent, or Firm—Robert R. Jackson

[57] ABSTRACT

A transfusion apparatus including a pump section for sequentially pressing and occluding a transfusion tube by means of a plurality of finger elements of a peristaltic type thereby to feed a liquid, a detecting section having (1) a circuit for detecting a given reference position of the pump section to generate a corresponding detection signal during periodic peristaltic movement of the pump section and (2) a circuit for detecting a working position of the pump section deviated from the reference position through the peristaltic movement thereby to generate a corresponding detection signal, and a drive controlling section for receiving the detected signals from the detecting section to compute and control the peristaltic rate thereby to maintain a constant delivery amount by the pump section.

3 Claims, 9 Drawing Figures

TRANSFUSION APPARATUS

FIELD OF THE INVENTION

This invention relates to a transfusion apparatus useful for an automatic dropper and the like.

BACKGROUND OF THE INVENTION

There ave hitherto been known peristaltic finger pumps as a transfusion apparatus useful for an automatic dropper (for example, Japanese Laid-open Patent Application No. 58-165868). In such finger pumps, a flexible transfusion tube is squeezed by movement of a plurality of finger elements in the liquid-feeding direction for supplying a constant amount of a liquid.

It has been found from determination of a flow rate on the delivery side of the pump that an approximately trapezoidal wave form of delivery and an approximately V-shaped wave form of back flow upon release of a pressing action byt he finger element on the tranfusion tube are repeated (see FIG. 5). Thus, the conventional finger pumps can not maintain a constant flow rate on the delivery side and therefore may not be readily utilized for the automatic dropper.

From this viewpoint, there have been various proposals for maintaining the constant flow rate on the delivery side in the peristaltic pumps for suc an application. For example, Japanese Utility Model Publication No. 57-27463 discloses a transfusion apparatus for preventing the back flow, in which a time point of releasing a complete occlusion of the transfusion tube through rotation of a pressing element of the peristaltic pump is detected to provide a signal which allows a driving motor of the pump to rotate for a predetermined period of time at a higher velocity than its normal rotation, thereby to supplement a back flow portion in a short time. However, if the proposed transfusion apparatus is applied in the peristaltic finger pump, the driving motor of the finger pump is rotated faster than the normal rotation from a time point of releasing the complete occlusion of the tube (point P), as shown in FIG. 5. It is true that the period of back flow is reduced, but the delivery flow rate is still somewhat stagnated and the stagnation may not be neglected especially at the lower driving velocity of the pump, resulting in difficulty of its application in the automatically dropping transfusion apparatus.

Accordingly, the automatic dropping transfusion apparatus requires a flow rate characteristic of the pump having a stable flow rate and an accurate infusion over the wide flow range for its use of injecting a pharmaceutical liquid into a human body. In particular, the stable flow rate in the lower flow range is highly desired for infants and serious patients. For example, the peristaltic finger pump shows an approximately trapezoidal wave form of delivery and an approximately V-shaped wave form of the back flow upon release of the pressing and occluding action of the finger elements on the transfusion tube, so that the flow rate characteristic cannot be constant. For this reason, the pump of such type requires a drive control capable of approaching not only the increasing and decreasing ranges of the flow rate in the trapezoidal wave form but also the back flow wave form toward a predetermined flow rate.

In accordance with the invention, as shown in FIG. 5, for the flow rate characteristic of delivery from the transfusion tube accompanied with a certain peristaltic movement of the finger elements in the conventional peristaltic finger pump, the maximum delivery amount ($DV_M$) of the trapezoidal wave form is set to a reference amount, and the instantaneous delivery amount (DVn) is determined at a given position (n). The peristaltic rate at this position is then set to be mutliplied by a factor of $DV_M/DVn$ in order to maintain the delivery amount at a constant value of $DV_m$ thereby to achieve the stable flow rate characteristic on the delivery side. The factor of $DV_M/DVn$ may be determined by previous experiments.

SUMMARY OF THE INVENTION

Accordingly, the transfusion apparatus of the invention comprises a pump section for sequentially pressing and occluding a transfusion tube by means of a plurality of finger elements of a peristaltic type thereby to feed a liquid, a detecting section having (1) a circuit for detecting a given reference position of the pump section to generate a corresponding detection signal during periodic peristaltic movement of the pump section and (2) a circuit for detecting a working position of the pumping section deviated from the reference position through the peristaltic movement thereby to generate a corresponding detection signal, said peristaltic movement being determined by said finger elements, and a drive controlling section for receiving the detected signals from the detecting section to compute and control the peristaltic rate thereby to maintain a constant delivery amount by the pump section.

In the transfusion apparatus according to the invention, it is preferred that a maximum delivery amount ($DV_M$) in an approximately trapezoidal wave form of delivery in the pump section is set to a reference amount, and that the drive controlling section is set to compute and control the peristaltic rate (Vn) at a given position established for an instantaneous delivery amount (DVn) in accordance with the following equation:

$$Vn = K \times DV_M/DVn \text{ (for } DVn > 0)$$

wherein K is a constant, n is 0, 1, 2, 3 - - -, and Vn does not exceed a given maximum rate but is a given maximum rate for $DVn \leq 0$.

In this case, the maximum rate is preferably maintained so as to offset a negative integrated amount of the delivery from a transition point of the instantaneous delivery amount (DVn) from negative to positive.

In accordance with the invention, the position of the periodic peristaltic movement of the pump section may be properly detected to provide the signal, from which the peristaltic rate may be computed for stabilizing the delivery flow rate in the total delivery cycle especially for the automatic dropper requiring a micro-flow rate characteristic, thereby to achieve high precision of feeding an infusion liquid.

The invention will now be described in more detail in the context of its preferred embodiments and with reference to the accompanying drawings.

PREFERRED EMBODIMENTS OF THE INVENTION

Figure 1:
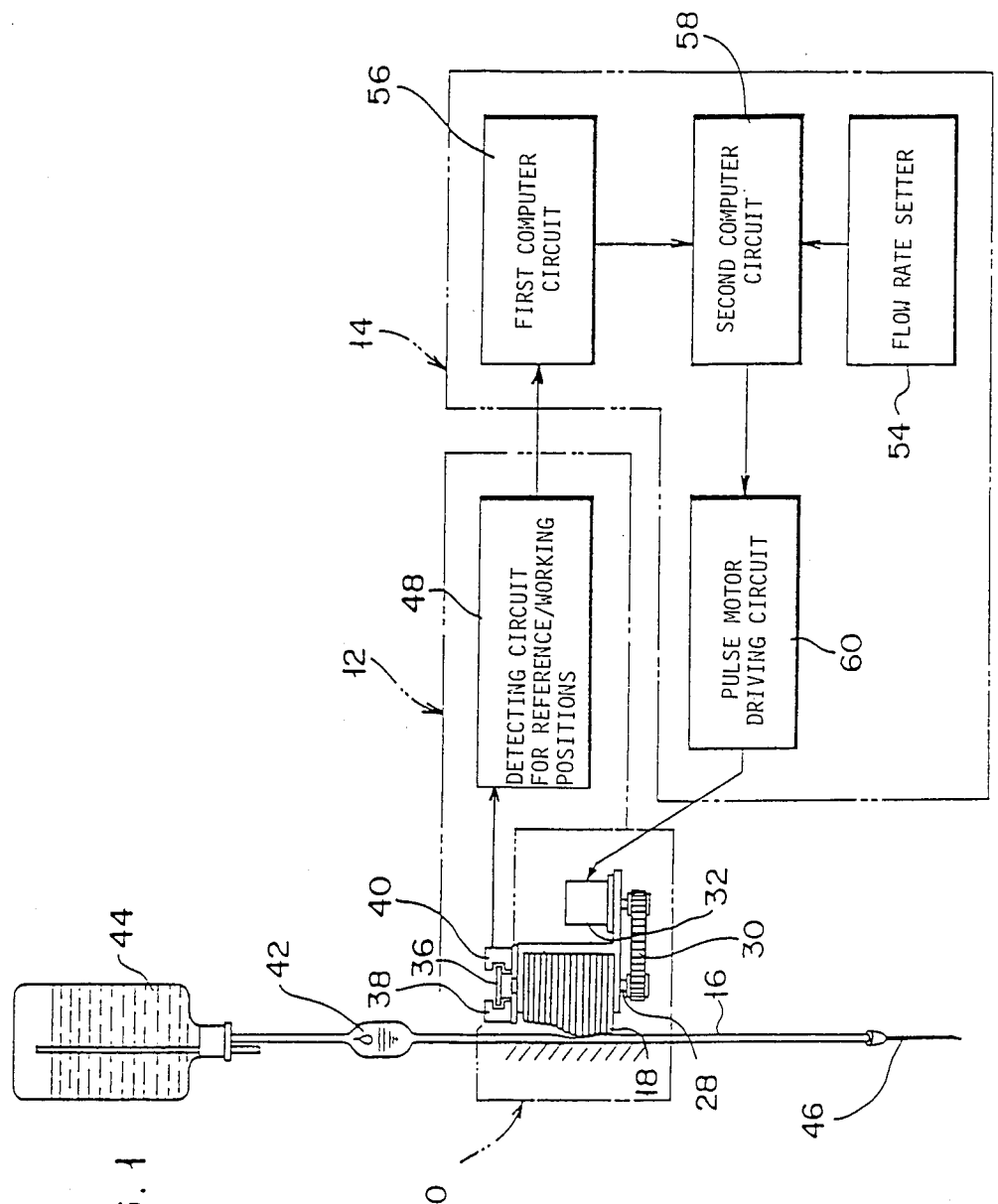
FIG. 1 is a system diagram of one embodiment of the transfusion appratus according to the invention.

FIG. 1 is a system diagram of one embodiment of the transfusion apparatus according to the invention, which comprises principally a pump section 10, a detecting section 12 and a drive controlling section 14.

Figure 2:
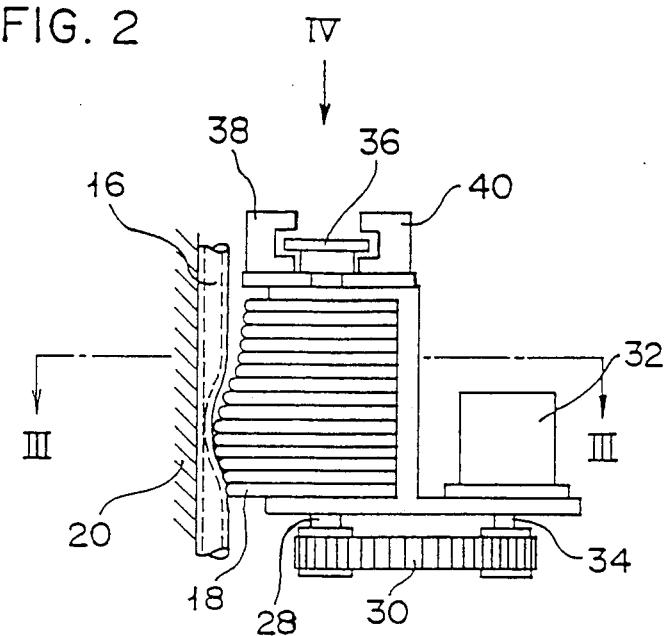
FIG. 2 is a partial sectional side view of the pump section in FIG. 1.
Figure 3:
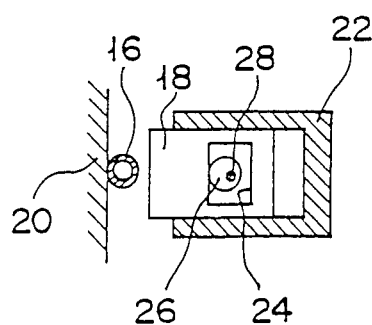
FIG. 3 is a sectional view taken along the line III—IJI in FIG. 2.
Figure 4:
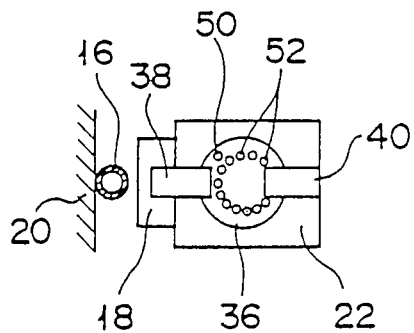
FIG. 4 is a side view as seen from the side IV of FIG. 2.
Figure 5:
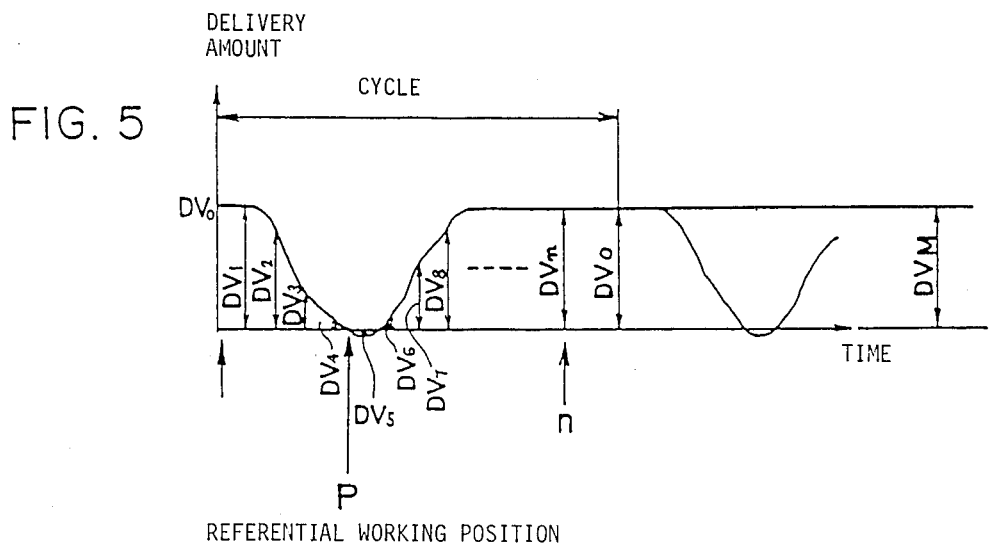
FIG. 5 is a wave form diagram showing the delivery flow characteristic of the transfusion apparatus in FIG. 1 when the peristaltic rate is set constant.

Pump section 10 comprises an elastic transfusion tube 16 made of vinylchloride or silicone, a plurality of peristaltic finger elements 18 disposed onone side of the transfusion tube 16 for sequentially occluding and opening tube 16, and a back plate 20 disposed oppositely to the finger elements 18 for securing the other side of the transfusion tube 16, as shown in FIG. 2. Each finger element 18 is supported by a holder 22 and provided with an elongated hole 24 for positioning therein an eccentric cam 26, through which is inserted a rotary shaft 28, thereby to generate the required peristaltic movement of the finger elements 18. Each eccentric cam 26 is arranged so as to be delayed at an angle of 360°/the number of cams relative to an adjacent upstream cam fixed to the same rotary shaft 28, so that a rotating movement of the eccentric cams may be converted to a linear movement of the finger elements 18 for urging and feeding a liquid in the transfusion tube 16. The rotary shaft 28 at its one end is connected through a transmission mechanism 30 to a driving shaft 34 of a pulse motor 32, while its other end is provided with a rotation-detecting disc 36 which cooperates with a detector 38 for detecting a reference position of the peristaltic movement and another detector 40 for detecting a rotation angle or a working position of the peristaltic movement from the reference position (see FIG. 4).

The transfusion tube 16 of the pump section 10 is connected on its upstream side through a dropping cylinder 42 to a bottle 44 of a pharmaceutical liquid, while on its downstream end tube 16 is provided with an injection needle 46. The detecting section 12 comprises a detector 38 for detecting the reference position, another detector 40 for detecting the working position, and a detecting circuit 48 for the reference/working positions. The detector 38 for the reference position is formed of a photo-electric detector which comprises a pair of light-emitting diodes for detecting an aperture 50 corresponding to the reference position on a single circumferential site of the rotationdetecting disc 36 and a photo-transistor, while the detector 40 for the working position comprises a similar photo-electric detector for detecting a plurality of apertures 52 equally spaced apart along a slightly inner circle relative to the aperture 50 on the disc 36. The detecting circuit 48 may generate a predetermined working signal which is based on the detected signals of the reference/working positions by the respective photo-electric detectors. Thus, the detecting section 12 has a function of transmitting the position of the peristaltic movement in the pump section 10 to the drive controlling section 14.

The drive controlling section 14 receives the signal from the detecting section 12 to recognize the position of the peristaltic movement in the pump section 10, and has data regarding the instantaneous delivery amount at that position, which has been previously determined by experiments, for computing and controlling a constant delivery amount. For this purpose, the drive controlling section 14 comprises a flow rate setter 54, a first computer circuit 56, a second computer circuit 58 and a pulse motor driving circuit 60. In the setter 54, the maximum delivery amount ($DV_M$) of the approximately trapezoidal wave form is set to the reference amount based on the flow rate characteristic of the transfusion tube derived from a given peristaltic movement in the pump section 10, while a ratio $DV_M/Dvn$ has been previously determined by experiments from data of the instantaneous delivery amount DVn at a given position (n). In the first computer circuit 56, a shift ratio Cn of the peristaltic movement may be computed depending on the working signal received from the detector 48 for maintaining the delivery amount at a constant level according to the following equation;

$$Dn = DV_M/DVn \tag{1}$$

In the second computer circuit 58, on the other hand, a velocity Vn of the peristaltic movement may be computed depending on the shift ratio Cn for ensuring the constant delivery amount according to the following equation;

$$Vn = K \times DV_M/Dvn \text{ (for } DVn > 0) \tag{2}$$

wherein K is a constant, n is 0, 1, 2, 3 - - - , and Vn does not exceed a given maximum rate but is a given maximum rate for $DVn \leq 0$.

The optimal velocity of the peristaltic movement Vn thus obtained is output as a signal for drive-controlling the pulse motor 32 through the pulse motor driving circuit 60.

Figure 6:
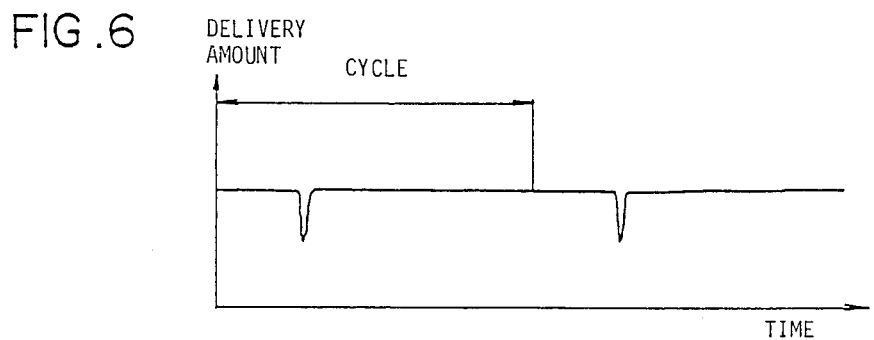
FIGS. 6 and 7 are wave form diagrams showing the delivery flow characteristic of the transfusion apparatus according to the invention.
Figure 7:
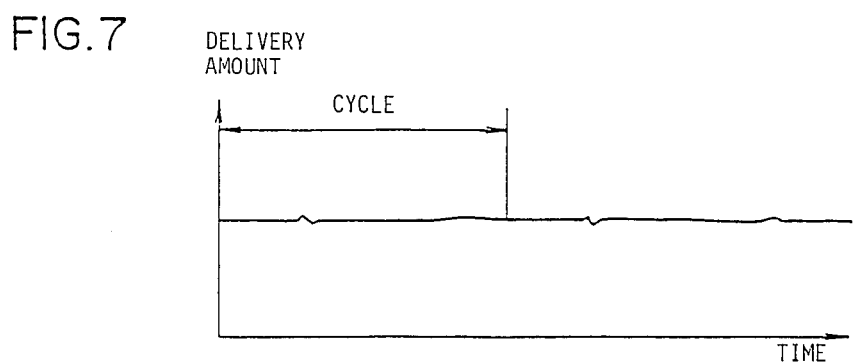

As a result, in the transfusion apparatus of this embodiment, the control of the shift ratio Cn represented by the equation (1) provides a curve of an actual delivery characteristic, as shown in FIG. 6. Further, if the maximum rate is maintained so as to offset a negative integrated amount of the delivery from a transition point of the instantaneous delivery amount (DVn) from negative to positive, then the actual delivery characteristic may be ideally and highly stable, as shown in FIG. 7.

Figure 8:
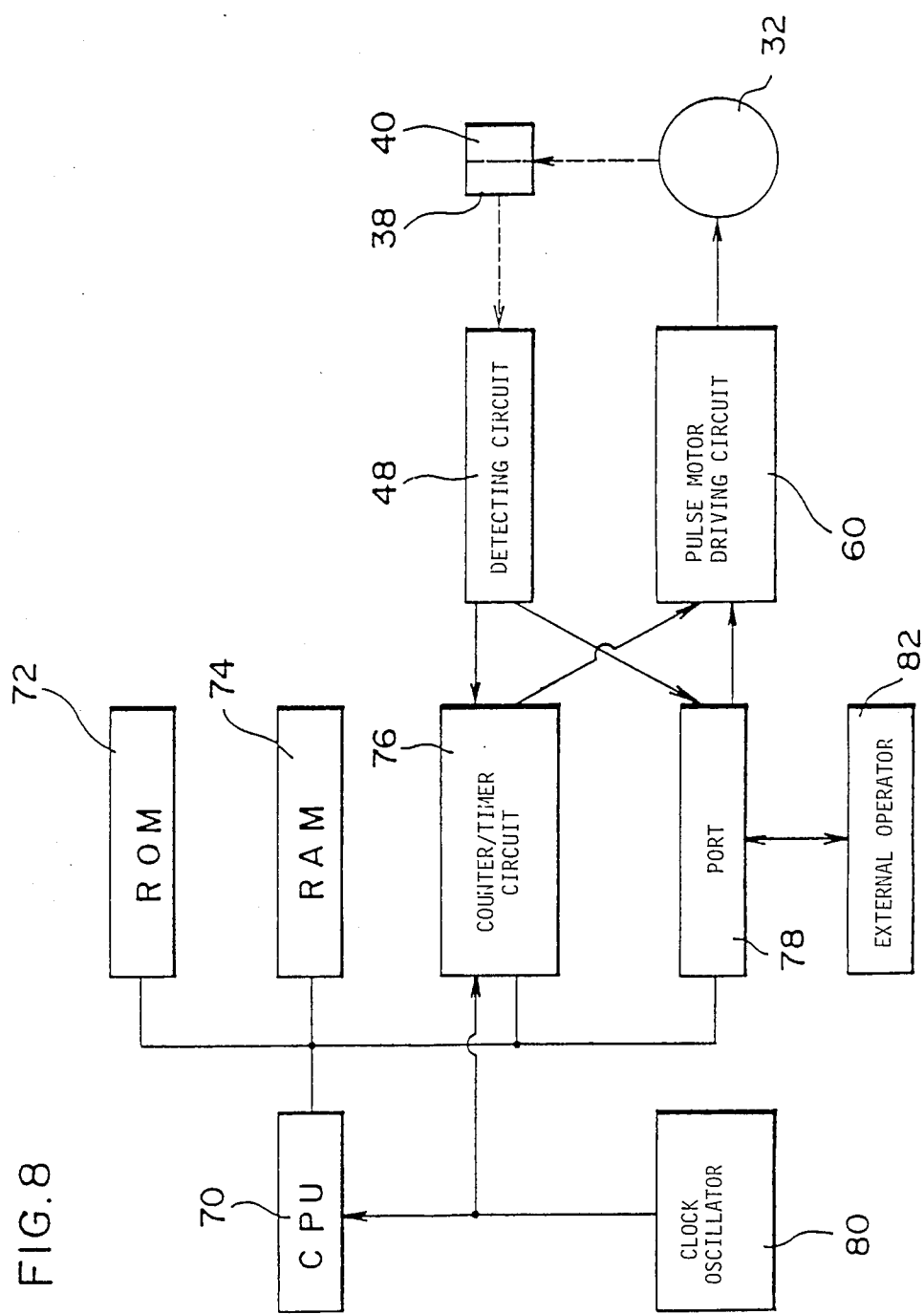
FIG. 8 is a block diagram of the micro-computerized drive controlling section of the transfusion apparatus according to the invention.

The transfusion apparatus according to the invention may utilize a micro-computer as the computer circuit for the drive controlling section 14 in the above embodiment. FIG. 8 shows a system comprising the microcomputer as the computer circuit, wherein reference 70 represents a CPU which is connected to ROM 72, RAM 74, a counter/timer circuit 76 and a I/O port 78, as well as an optional clock oscillator 80. Further, the counter/timer circuit 76 and the I/O port 78 are connected to the detector 48 for the reference/working positions and the pulse motor driving circuit 60, while the I/O port 78 is connected to an external operating device 82 capable of externally inputting and monitoring. With such construction of the system, the calculation and the control for driving the pulse motor 32 may be readily achieved in the drive controlling section 14.

Figure 9:
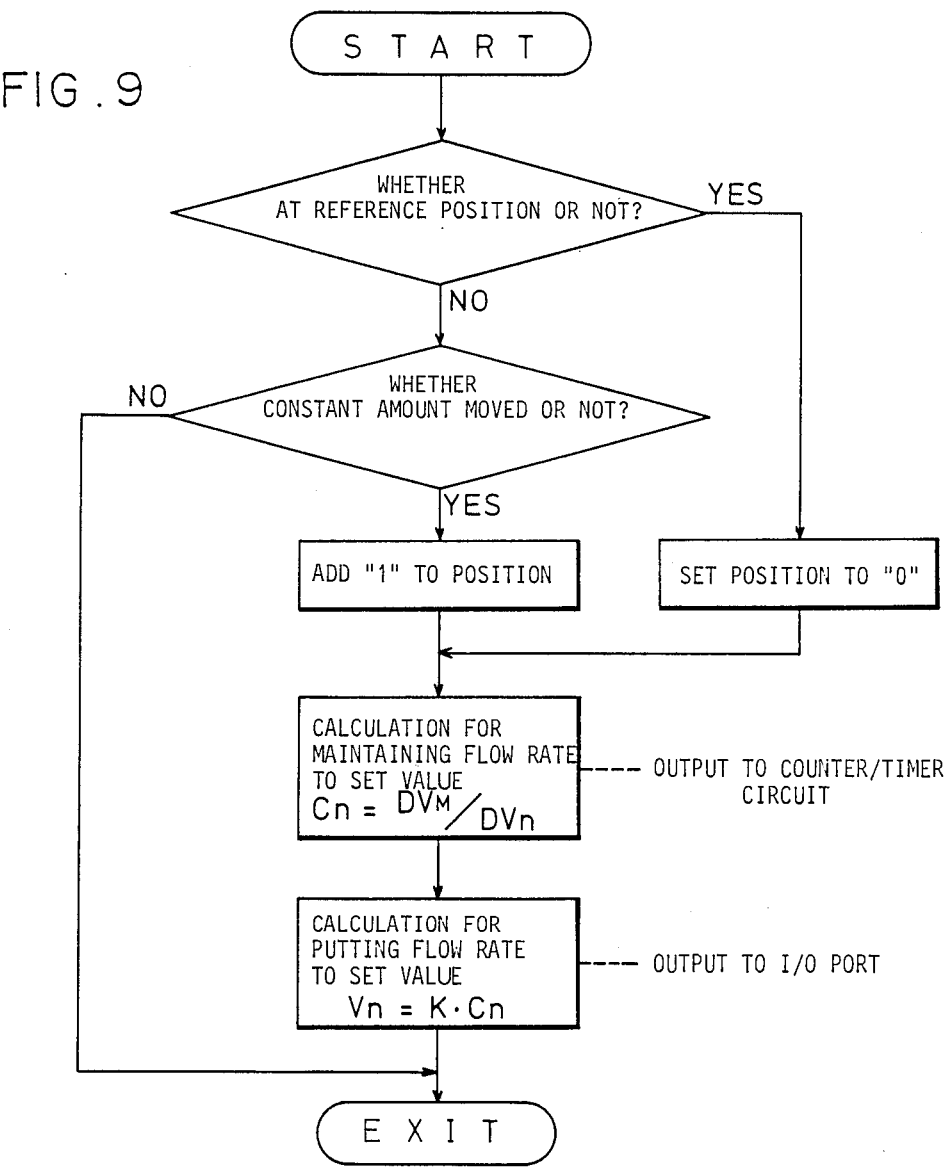
FIG. 9 is a flow chart for operating the system of FIG. 8.

One example of a flow chart for operating the above system is shown in FIG. 9. At first, various setting values, equations for calculation and system-controlling programs are stored in the CPU 70, the ROM 72 and the RAM 74 for determining if the peristaltic movement of the pump section is located at the reference position in relation to the signal received from the detecting circuit 48 through the I/O port 78. If it is located on the reference position, then the position is set to 0 (zero point) and the calculation of the first computer circuit 56 (according to the equation (1)) is carried out, followed by the calculation of the second computer circuit 58 (according to the equation (2)), and the resultant values are fed throught the I/O port 78 to the pulse motor driving circuit 60. Thereafter, a given working position of the peristaltic movement in the pump section is recognized and the same procedure of the calculation is repeated each time for feeding the controlling signal to the pulse motor driving circuit 60 through the I/O port 78.

With the transfusion apparatus thus constructed, the driving control of the pump section may be readily, accurately and programmably realized depending on its purpose of application.

It will be appreciated from the above embodiments that in accordance with the invention the transfusion tube may be pressed and occluded with its tip envelope being deformed by the plurality of the peristaltic finger elements, and that the rate of the peristaltic movement may be shifted so as to maintain the constant delivery flow rate and the minute variaton of the delivery flow rate.

In particular, the transfusion apparatus according to the invention, compared with the conventional apparatus, has the stable delivery characteristic for the microtransfusion at the low driving velocity of the pump section and is thus very useful for the automatic dropper.

Although the invention has been described hereinabove with reference to the preferred embodiments, it will be appreciated that many variations and modifications may be made without departing from the spirit and the scope of the invention.

What is claimed is:

1. Transfusion apparatus comprising:
a finger-type peristaltic pump including (1) a resilient, longitudinal transfusion tube containing liquid to be fed by the transfusion apparatus, (2) a plurality of finger elements disposed in a series along the longitudinal axis of said transfusion tube, and (3) drive means for momentarily actuating said finger elements one after another in a recurrent succession so that the actuated finger elements press on and occlude said transfusion tube and cause the liquid in said tube to move longitudinally along the tube ahead of the actuated finger elements;

means responsive to said peristaltic pump for producing a reference position indicating output signal each time the finger elements of said pump reach a predetermined reference point in said recurrent succession, and for producing a succession of working position indicating output signals each indicating that said recurrent succession has progressed a predetermined increment beyond said reference point; and drive control means responsive to said reference and working position indicating output signals for determining the rate at which said finger elements must be actuated at the point in said recurrent succession at which said reference and working position indicating signals indicate that the pump currently is in order to maintain a constant liquid delivery amount of the pump and for causing said drive means to actuate said finger element at that rate.

2. Transfusion apparatus according to claim 1, wherein when said drive means is operated at a constant rate, the pump delivers the liquid with an approximately trapezoidal wave form having an instantaneous delivery amount $DVn$ and a maximum delivery amount $DV_M$, and wherein the drive control means controls the rate $Vn$ at which said drive means actuates said finger elements in accordance with the following equation:

$$Vn = K \times DV_M / DVn \text{ (for } DVn > 0)$$

wherein K is a constant, n is 0, 1, 2, 3 - - - indicating how many increments beyond said reference point said pump currently is, and Vn does not exceed a predetermined maximum rate but is said maximum rate for $DVn \leq 0$.

3. Transfusion apparatus according to claim 2, wherein when said drive means is operated at a constant rate, said trapezoidal wave form includes at least some negative values of DVn, and wherein said drive control means maintains said maximum rate for a sufficient period of time to offset the negative integrated liquid delivery amount associated with said negative values of DVn as DVn goes from negative to positive.

* * * * *